United States Patent [19]

Noguchi et al.

[11] Patent Number: 5,968,492

[45] Date of Patent: Oct. 19, 1999

[54] HAIR CARE PRODUCTS

[75] Inventors: Yasunobu Noguchi; Tatsuru Tabohashi, both of Kawasaki, Japan

[73] Assignee: Ajinomoto Co., Inc., Tokyo, Japan

[21] Appl. No.: 08/921,599

[22] Filed: Sep. 2, 1997

[30] Foreign Application Priority Data

Aug. 30, 1996 [JP] Japan ................................... 8-246885
Aug. 4, 1997 [JP] Japan ................................... 9-208897

[51] Int. Cl.$^6$ ............................... A61K 7/075; A61K 7/06
[52] U.S. Cl. ....................................... 424/70.1; 424/70.11
[58] Field of Search ................................ 424/70.1, 70.11

[56] References Cited

U.S. PATENT DOCUMENTS

| 4,032,676 | 6/1977 | Heins et al. ............................ 424/273 |
| 5,028,416 | 7/1991 | Yano et al. ............................... 424/59 |

FOREIGN PATENT DOCUMENTS

| 0788832 A1 | 8/1977 | European Pat. Off. . |
| 0336265 A2 | 10/1989 | European Pat. Off. . |
| 0738710 A1 | 10/1996 | European Pat. Off. . |
| 48 022 417 | 3/1973 | Japan . |
| 48 072 118 | 9/1973 | Japan . |
| 355053251 | 4/1980 | Japan . |
| 409271655 | 10/1997 | Japan . |
| 10072331 | 3/1998 | Japan . |

OTHER PUBLICATIONS

Database WPI, Section Ch, Week 9311, Derwent Publications Ltd., London, GB; Class D21, AN 93–088574, XP002053600 & JP 05 032 529 A (Mitsubishi Petrochemical Co., Ltd), Feb. 9, 1993, abstract.

Patent Abstracts of Japan vol. 010, No. 350 (C–387), Nov. 26, 1986 & JP 61 151109 A (Lion Corp), Jul. 9, 1986, abstract.

*Primary Examiner*—Sally Gardner-Lane
*Attorney, Agent, or Firm*—Oblon, Spivak, McClelland, Maier & Neustadt, P.C.

[57] ABSTRACT

A composition suitable for hair care which has excellent hair conditioning effects and provides a pleasant sensory feeling during use. The composition contains basic amino acids and high alcohols, and is preferably free of non-polymeric alkyl quaternary ammonium salts, which are irritating and poorly biodegradable. The composition may also contain cationic polymers to enhance the conditioning effects. Anionic surface active agents, ampholytic surface active agents, or both, may also be incorporated into the hair care composition in order to impart hair cleansing properties.

22 Claims, No Drawings

HAIR CARE PRODUCTS

BACKGROUND OF THE INVENTION

1. Field of the Invention

The present invention relates to a hair care composition product containing (A) a basic amino acid derivative and (B) a higher alcohol as active ingredients. The composition may optionally contain (C) a cationic polymer and/or (D) an anionic surface active agent, an ampholytic surface active agent, or both, as additional active ingredients. The composition may be used, for example, to condition hair. The composition makes hair easier to comb, imparts a soft and moist feeling to the hair, and provides good sensory feel properties during use.

2. Discussion of the Background

When the hair is washed with a soap, a synthetic wash, detergent and the like, excess fat is removed during washing. As a result, the hair loses smoothness, a dry and hard feeling is produced, the combing property is decreased, and broken hair or split hair may be produced.

In order to eliminate these drawbacks, a hair care composition product, such as a shampoo or a rinse, contains ingredients that provide hair conditioning effects. Such a hair care composition which is most widely used is one containing a quaternary ammonium salt, such as a dialkyldimethylammonium chloride or a monoalkyltrimethylammonium chloride, as the main active ingredient.

These alkyl quaternary ammonium salts are electrically adsorbed on the surface of the hair, which is weakly acidic, whereby a good combing property and smoothness is imparted to the hair. However, the skin and the mucous membrane are heavily irritated by these salts, and the biodegradability thereof is poor.

Further, when the alkyl quaternary ammonium salts are used in combination with an anionic surface active agent, a water-insoluble salt is formed, decreasing solubility and sensory feeling during use. Thus, the use of the alkyl quaternary ammonium salts is limited when incorporating the same into a hair care composition, so the development of conditioning agents which may replace the alkyl quaternary ammonium salts has been in demand.

Known examples of conditioning agents other than the alkyl quaternary ammonium salts include alkylamideamine salts such as stearic acid diethylaminoethylamide and cocoyl arginine ethyl ester pyrrolidone carboxylate. These compounds exhibit low irritation and an excellent biodegradability, but have poor conditioning effects.

In recent years, consumers have had much interest in safety and environmental issues, and a hair care composition which has excellent conditioning properties and provides acceptable sensory feelings feeling during use which does not require alkyl quaternary ammonium salts have been in high demand.

SUMMARY OF THE INVENTION

It is an object of the present invention to provide a hair care product which provides excellent hair conditioning effects and sensory feeling during use, and does not require alkyl quaternary ammonium salts.

It is another object of the present invention to provide a hair care composition which can be used to cleanse and condition hair.

The present inventors have found that the above objects and others are accomplished with a composition suitable for hair care which contains:

(A) at least one basic amino acid derivatives represented by formula (1) or a salt thereof

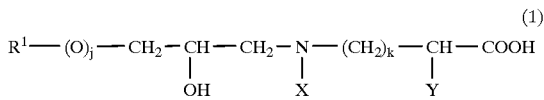

where
$R^1$ is a linear or branched alkyl or alkenyl group having from 8 to 22 carbon atoms,
j is 0 or 1,
X is a hydrogen atom or a substituent represented by formula (2)

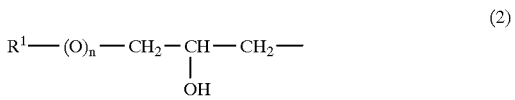

in which
n is 0 or 1,
k is an integer from 0 to 5, and
when k is 0, Y is a substituent represented by formula (3)

in which
m is an integer from 1 to 5, and
Z is one of the following substituents (a) to (d)

when k is an integer of from 1 to 5, Y is an amino group; and (B) at least one higher alcohol.

Further, the present invention also relates to a composition additionally containing (C) at least one cationic polymer and/or (D) at least one anionic surface active agent, an ampholytic surface active agent, or both, in addition to (A) and (B) as active agents. The present invention also relates to methods of conditioning and/or cleansing hair using the hair care composition of the present invention.

A more complete appreciation of the invention and many of the attendant advantages thereof will be readily obtained as the same becomes better understood by reference to the following detailed description.

DESCRIPTION OF THE PREFERRED EMBODIMENTS

The hair care composition product of the present invention provides excellent conditioning properties and sensory feelings during use. Since these properties may be attained without non-polymeric alkyl quaternary ammonium salts, which are problematic in the terms of irritation and biodegradability, the composition of the present invention may be substantially free of these materials, in a preferred embodiment. The term "substantially free" means that the composition contains, most preferably, no non-polymeric alkyl quaternary ammonium salts, more preferably at most 1% by weight and, preferably, at most 2% by weight.

The basic amino acid derivatives of formula (1), which are component (A) in present composition, may be formed by reacting a basic amino acid with a glycidyl ether represented by formula (4)

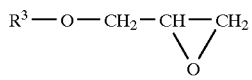  (4)

where $R^3$ represents a linear or branched alkyl or alkenyl group having from 8 to 22 carbon atoms, or an epoxy alkane represented by formula (5)

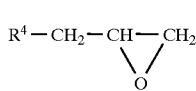  (5)

where $R^4$ represents a linear or branched alkyl or alkenyl group having from 8 to 22 carbon atoms, under alkaline conditions in a lower alcohol or a mixed solvent of a lower alcohol and water. For example, the reaction of an amino acid with an epoxy alkane is described in Japanese Laid-Open (Kokai) No. 22,417/1973.

Regarding the basic amino acid derivatives of formula (1), a compound obtained by the reaction of a glycidyl ether with a basic amino acid is preferable to a compound obtained by the reaction of an epoxy alkane with a basic amino acid. Amino acid derivatives obtained by reacting a neutral or acidic amino acids with a glycidyl ether or an epoxy alkane generally do not have desired hair conditioning properties.

The glycidyl ether of formula (4) can be formed, for example, by reacting a saturated or unsaturated natural or synthetic higher alcohol with epichlorohydrin. Specific examples thereof include decyl glycidyl ether, dodecyl glycidyl ether, tetradecyl glycidyl ether and stearyl glycidyl ether. It may be used either alone or in admixture of two or more at a variable ratio. Examples of commercially available glycidyl ethers include "Epiol L-41" and "Epiol SK" (trade names for decyl glycidyl ether and stearyl glycidyl ether made by NOF Corporation, respectively), "Heloxy 8" (trade name for a mixture of dodecyl glycidyl ether and tetradecyl glycidyl ether made by ACI Japan, Ltd.), "Denacol EXAMINER-192" (trade name for a mixture of dodecyl glycidyl ether and tetradecyl glycidyl ether made by Nagase Chemicals, Ltd., and "SY-25L" (trade name for a mixture of decyl glycidyl ether and dodecyl glycidyl ether made by Sakamoto Yakuhin Kogyo Co., Ltd. As the epoxy alkane of formula (5), the "AOEX Series" made by Daicel Chemical Industries, Ltd. may be used.

As the basic amino acid, natural and synthetic amino acids may be employed. Examples thereof include arginine, lysine, ornithine, histidine, hydroxy lysine, and $\alpha,\gamma$-diaminobutyric acid. Arginine and lysine are preferable, and arginine is especially preferred. Mixtures of different basic amino acids may be used. Either D- or L-stereoisomers of these amino acids may be used. Mixtures of stereoisomers may also be used. Accordingly, the optical purity may range from 0% ee (i.e., a racemate) to 100% ee.

In the case of lysine and ornithine as basic amino acids, the coupling site with the glycidyl ether or the epoxy alkane is preferentially the $\epsilon$-amino group or the $\delta$-amino group. It may also be the $\alpha$-amino group. Further, a compound obtained by reacting two molecules of a glycidyl ether or an epoxy alkane with an $\epsilon$-amino group, a $\delta$-amino group or an $\alpha$-amino group may also be used. Still further, a compound obtained by reacting one molecule thereof with an $\epsilon$-amino group of lysine (or the $\delta$-amino group of ornithine) and one molecule with an $\alpha$-amino group, and a compound formed by adding three or four molecules of a glycidyl ether to one molecule of an amino acid may also be used. However, a compound obtained by reacting one molecule of basic amino acid with one molecule of glycidyl ether or epoxy alkane is especially preferable.

In the reaction of a glycidyl ether or an epoxy alkane with the amino acid, it is preferable that an amino acid is used as an alkali metal salt or is reacted under an alkaline condition to enhance the reactivity and prevent side reactions. However, in the case of arginine, the reaction may be conducted without using these conditions.

Examples of the reaction solvent include lower alcohols such as methyl alcohol, ethyl alcohol, n-propyl alcohol and i-propyl alcohol, and a mixed solvent of the lower alcohol and water. The mixing ratio of the lower alcohol to water varies depending on the types of an amino acid and a glycidyl ether or an epoxy alkane. The ratio of the lower alcohol to water is usually between 100:0 and 10:90, preferably between 1:1 and 2:1. When the proportion of alcohol is low, the solubility of a glycidyl ether or an epoxy alkane is decreased, notably reducing the reaction rate.

The reaction temperature may vary depending on the type and the composition of the reaction solvent. It is usually between 70° C. and 100° C., preferably between 80° C. and 95° C. It is preferable to conduct the reaction under reflux. The glycidyl ether or the epoxy alkane may be added at once before heating, or in divided portions or dropwise continuously after starting the heating. In order to suppress the formation of by-products, it is preferable to add the same dropwise continuously after starting the heating.

The product obtained by the reaction of the glycidyl ether or the epoxy alkane with the basic amino acid is usually not a single compound but rather a mixture formed by adding one or two molecules of the epoxy alkane to one molecule of the basic amino acid. It is possible that this mixture be isolated into each single compound through, for example, chromatography and one or more of such single compounds are used as a starting material for the hair care product of the present invention, or that the mixture is used as such. Further, unreacted basic amino acids may be present in the mixture.

The reaction mixture formed by reacting the glycidyl ether or the epoxy alkane with the basic amino acid can be used as a starting material for the composition of the hair care product in the present invention as such without conducting any purification or by conducting purification to such an extent that the reaction solvent is distilled off as required. For example, in case of using ethyl alcohol or the like as a reaction solvent, it may be present in the reaction mixture which is used as a starting material for the composition of the hair care product provided it does not significantly impairs the hair conditioning effect. However, when the reaction solvent contains methyl alcohol, this alcohol component is preferably removed before formulating the composition.

Examples of the salts of the basic amino acid derivatives of formula (1) include inorganic acid salts such as hydrochlorides, sulfates and phosphates; and organic acid salts such as acetates, citrates, p-toluene sulfonates, tartrates, an acidic amino acid salt, and an L- or DL-pyrrolidone carboxylate.

The basic amino acid derivatives of formula (1) exhibit low irritation and have high biodegradability as compared to the conventional alkyl quaternary ammonium salts. However, with only the basic amino acid derivatives, the conditioning effects are not necessarily satisfactory, nor are the sensory feelings during use desirable.

As a result of further investigations, it was found that the combined use of the basic amino acid derivatives and higher alcohols as a second essential component could further increase the conditioning effects and improve the sensory feelings during use of the product. Preferably, the higher alcohol has at least 12 carbon atoms. This alcohol may have more than one hydroxyl group, e.g., two, three or four, or more hydroxyl groups, however, one hydroxyl group is preferred.

A higher alcohol represented by formula (6) is particularly preferred:

$$R^5\text{—OH} \qquad (6)$$

where $R^5$ represents a linear or branched alkyl or alkenyl group having from 12 to 36 carbon atoms. In the present invention, a branched alkyl includes groups which contain a cyclic moiety therein. Alkenyl groups have at least one double bond. A higher alcohol containing an alkyl group having from 14 to 22 carbon atoms is very particularly preferred. Specific examples of such a higher alcohol include cetyl alcohol, stearyl alcohol, behenyl alcohol, isostearyl alcohol, octyldodecanol and oleyl alcohol. The higher alcohols may be used either singly or in combination.

The basic amino acid derivatives of formula (1) provide, as stated above, a low degree of irritation as compared to the conventional alkyl quaternary ammonium salts, and they provide a hair care product with excellent conditioning properties. Especially in recent years, consumers' interest about safety and environmental problems are increasing. Accordingly, improved hair care products may be prepared with these basic amino acid derivatives. However, with only these basic amino acid derivatives, the conditioning effects are not necessarily satisfactory, and the sensory feeling during use may be unsatisfactory. However, when the basic amino acid derivatives of formula (1) and/or salts thereof are used in combination with the higher alcohol as in the present invention, it is possible to increase the conditioning effects and the sensory feeling during conditioning of the hair.

The amount of component (A) in the composition of the hair care product of the present invention may be appropriately determined depending on the desired product and is not especially limited. It is preferably from 0.1 to 10% by weight, and more preferably from 1 to 5% by weight, based on the total weight of the composition. These ranges include all specific values and subranges therebetween, including 0.5, 2, 3, 4 and 8% by weight. When it is less than 0.1% by weight, the conditioning effect may be unsatisfactory in some cases. When it exceeds 10% by weight, hair may have an unlubricated or tacky feeling in some cases.

The amount of component (B) in the composition may vary widely. It is preferably from 0.1 to 30% by weight, and more preferably from 2 to 20% by weight. These ranges include all specific values and subranges therebetween, including 0.2, 0.5, 1, 5, 10, 15 and 25% by weight. When it is less than 0.1% by weight, the hair conditioning effect may be insufficient in some cases. When it exceeds 30% by weight, the sensory feeling during use may be reduced in some cases.

Further, the ratio of component (B) to component (A) in the composition of the present invention may vary over a wide range and it is not especially limited. The weight ratio of component (B) to component (A) is preferably from 10:100 to 100:0.5, more preferably from 50:100 to 100:5. These ranges include all specific values and subranges therebetween.

The conditioning effects of the composition of the hair care product may be further be increased by incorporating a cationic polymer as component (C) into the composition, in addition to components (A) and (B). Examples of the cationic polymer include quaternary nitrogen-substituted cellulose ether derivatives, quaternary nitrogen-containing poly(trialkylaminoethyl methacrylate) derivatives, a water-soluble polymer of tetraethylenepentamine and epichlorohydrin, quaternary nitrogen-containing polyvinylpyrrolidone, and cyclic cation group-containing polymers such as a diallyl quaternary ammonium homopolymer and a diallyl quaternary ammonium copolymer.

Suitable examples of commercially available products thereof are mentioned below. Examples of the quaternary nitrogen-substituted cellulose ether derivatives include polymer "JR-125", "JR-400" and "JR-30M" (made by Union Carbide Japan K.K.). Examples of the quaternary nitrogen-containing poly(trialkylaminoethyl methacrylate) derivatives include "Sumiflock" (made by Sumitomo Chemical Company Limited). Examples of the water-soluble polymer of tetraethylenepentamine and epichlorohydrin include "Nalco 600" (made by Nalco Japan Co., Ltd.). Examples of polyethyleneimine include "Epomin" (made by Nippon Shokubai Co., Ltd.). Examples of the cyclic cation group-containing polymer include "Merquat 100" and "Merquat 550" (made by Calgon Corporation). These cationic polymers can be used either singly or in combination.

The amount of component (C) in the hair care composition of the present invention may be determined depending on the desired product. It is preferably from 0.1 to 10% by weight, more preferably from 0.3 to 5% by weight. These weight percent ranges for (C) in the composition include all specific values and subranges therebetween, including 0.2, 0.5, 1, 2, 3, 4, 6, 7, 8 and 9% by weight, based on the total weight of the composition. When the amount of (C) is less than 0.1% by weight, the conditioning effects of the cationic polymer may not be significant. When it is more than 10% by weight, a rough feeling or a stickiness may occur during conditioning of the hair.

Cleansing properties may be imparted to the composition by incorporating an anionic surface active agent and/or an ampholytic surface active agent as component (D) into the composition, in addition to Components (A) and (B). The resulting product may be used for both conditioning and cleansing the hair, such as a rinse shampoo, a conditioning shampoo or the like. Further, the basic amino acid derivatives of formula (1) and salts thereof are soluble in the presence of the anionic surface active agent. When the basic amino acid derivatives of formula (1) and salts thereof are used with the anionic surface active agent, the problems related to solubility and sensory feelings associated with the alkyl quaternary ammonium salts are avoided.

Examples of the anionic surface active agent include carboxylic acid salt-type, sulfonic acid salt-type and sulfuric acid ester salt-type anionic surface active agents.

Examples of the carboxylic acid salt-type anionic surface active agent include N-acylaminocarboxylic acid salt-type and ether carboxylic acid salt-type surface active agents.

In the N-acylaminocarboxylic acid salt-type anionic surface active agent, the acyl group may be an acyl residue of a saturated or unsaturated fatty acid having from 8 to 22 carbon atoms. Examples thereof include acyl residues of fatty acids of a single composition, such as lauric acid, myristic acid, palmitic acid, stearic acid and oleic acid. Also available are acyl residues of natural mixed fatty acids such as a coconut oil fatty acid, a tallow fatty acid, a hardened tallow fatty acid, a castor oil fatty acid, an olive oil fatty acid and a palm oil fatty acid, and of synthetic fatty acids (including branched fatty acids). Examples of an aminocarboxylic acid that is bound thereto include acidic amino acids such as glutamic acid, aspartic acid, cysteic acid and homocysteic acid; neutral amino acids such as glycine, alanine, valine, leucine, isoleucine, phenylalanine, tryptophan, sarcosine, β-alanine, γ-aminobutyric acid, ε-aminocaproic acid, serine, homoserine, tyrosine, proline, hydroxyproline, cystine, cysteine and methionine; and basic amino acids such as lysine, ornithine and arginine. These acylaminocarboxylic acids can be used in the form of both optically active compounds and racemic compounds. Accordingly, the optical purity may range from 0 to 100% ee.

Examples of the ether carboxylic acid salt-type anionic surface active agent include a polyoxyethylene alkyl ether acetic acid salt and a polyglyceryl alkyl ether acetic acid salt. Specific examples thereof include polyoxyethylene lauryl ether acetic acid salt and polyoxyethylene tridecyl ether acetic acid salt.

Examples of the sulfonic acid salt-type anionic surface active agent include monobasic acid organic sulfonic acid salt-type anionic surface active agents such as sulfosuccinic acid salt-type, alkyl sulfonic acid salt-type, ester sulfonic acid salt-type and N-acyl sulfonic acid salt-type surface active agents.

Examples of the sulfosuccinic acid salt-type anionic surface active agent include a sulfosuccinic acid ester of a higher alcohol or its ethoxylate and a sulfosuccinic acid ester derived form a higher fatty acid amide represented by the following formulas (7) and (8), and salts thereof:

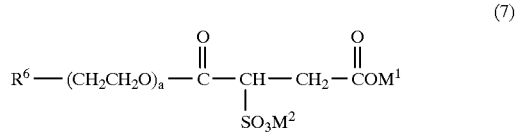

(7)

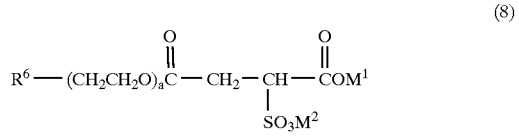

(8)

where

R$^6$ represents R$^7$—O— or R$^8$—CONH— in which R$^7$ represents a linear or branched alkyl or alkenyl group having from 8 to 22 carbon atoms, and R$^8$ represents a linear or branched alkyl or alkenyl group having from 7 to 21 carbon atoms, M$^1$ and M$^2$ are each, independently, a hydrogen atom, an alkali metal ion, an alkaline earth metal ion, an ammonium ion or organoaluminum ion, and a is an integer from 0 to 20.

Specific examples thereof include undecylenoylamidoethyl sulfosuccinic acid salt, sulfosuccinic acid polyoxyethylene lauroylethanolamide ester salt, sulfosuccinic acid lauryl salt, polyoxyethylene sulfosuccinic acid lauryl salt and oleic acid amide sulfosuccinic acid salt.

Examples of the monobasic acid organic sulfonic acid salt-type anionic surface active agent include a sulfonic acid salt containing a linear or branched alkyl or alkenyl group having from 8 to 22 carbon atoms, an alkylbenzenesulfonic acid salt containing a linear or branched alkyl group having from 10 to 16 carbon atoms, and an N-acyl sulfonic acid salt or an O-acyl sulfonic acid salt in which the acyl group is a linear or branched saturated or unsaturated fatty acid residue containing from 8 to 22 carbon atoms.

Specific examples thereof include an alkane sulfonic acid salt, an α-olefin sulfonic acid salt, an alkylbenzenesulfonic acid salt, an acylmethyltaurine salt, an isethionic acid fatty acid ester salt and an α-sulfonated fatty acid ester salt.

Examples of the sulfuric acid ester salt-type anionic surface active agent include alkyl sulfuric acid salt-type and ether sulfuric acid salt-type surface active agents.

The alkyl sulfuric acid salt-type anionic surface active agent is an ester of a linear or branched saturated or unsaturated higher alcohol having from 8 to 22 carbon atoms and sulfuric acid. Examples thereof include lauryl sulfuric acid salt, myristyl sulfuric acid salt and oleyl sulfuric acid.

The ether sulfuric acid salt-type anionic surface active agent is an alkylene oxide adduct of the above-mentioned alkyl sulfuric acid salt. Examples thereof include polyoxyethylene lauryl ether sulfuric acid salt, polyoxyethylene myristyl ether sulfuric acid salt and polyoxyethylene oleoyl ether sulfuric acid salt.

Examples of the basic component of these anionic surface active agents include alkali metals (such as sodium and potassium); alkaline earth metals (such as magnesium and calcium); organic amines (such as monoethanolamine, diethanolamine, triethanolamine, 2-amino-2-methyl-1-propanol and 2-amino-2-methyl-1,3-propanediol); basic amino acids (such as lysine, ornithine and arginine); and ammonia. These basic components can be used either singly or in combination.

These anionic surface active agents can be used either singly or in combination.

Examples of the ampholytic surface active agent include a betaine-type ampholytic surface active agent and an imidazoline-type ampholytic surface active agent.

Examples of the betaine-type ampholytic surface active agent include a carbobetaine-type ampholytic surface active agent, an amidobetaine-type ampholytic surface active agent, a sulfobetaine-type ampholytic surface active agent, a hydroxy sulfobetaine-type ampholytic surface active agent, an amidosulfobetaine-type ampholytic surface active agent and a phosphobetaine-type ampholytic surface active agent.

Such a betaine-type ampholytic surface active agent is, in other words, a betaine-type surface active agent containing an alkyl, alkenyl or acyl group having from 8 to 24 carbon atoms. Specific examples thereof include a coconut oil alkyldimethylaminoacetic acid betaine, a coconut oil fatty acid amidopropyldimethylaminoacetic acid betaine, stearyldihydroxyethylaminoacetic acid betaine, laurylhydroxysulfobetaine, laurylsulfobetaine, and laurylphosphobetaine. These betaine-type surface active agents can be used either singly or in combination.

Examples of the imidazoline-type surface active agent include 2-alkyl-N-carboxymethyl-N-hydroxyethylimidazolinium betaine, 2-alkyl-N-carboxyethyl-N-hydroxyethylimidazolinium betaine and 2-alkyl-N-sodium carboxymethyl-N-carboxymethyloxyethylimidazolinium betaine which contain an alkyl group having from 8 to 22 carbon atoms. These can be used either singly or in combination.

These ampholytic surface active agents may be used either singly or in combination.

The above-mentioned anionic surface active agent and ampholytic surface active agent can be used either singly or in combination.

In the composition of the present invention, the cationic polymer as component (C) may be used in combination with components (A), (B) and (D). When component (D) is an anionic surface active agent, it may form a water-insoluble salt with the cationic polymer as component (C). However, since the basic amino acid derivatives as component (A), which is a conditioning component, generally does not form such a salt, the conditioning effects may not be impaired. Accordingly, components (C) and (D) may be used in together in the composition, provided that the sensory feelings during use are still acceptable.

The amount of component (D) in the composition of the present invention may vary depending on the desired product. It is usually from 0.1 to 70% by weight, preferably from 0.1 to 50% by weight, more preferably from 0.1 to 30% by weight. These weight percent ranges for (D) in the composition include all specific values and subranges therebetween, including 0.5, 1, 10, 15, 20, 25, 35, 40, 45, 50, 55, 60 and 65% by weight, based on the total weight of the composition. When the amount of (D) is less than 1% by weight, the washing effect may not be satisfactory in some cases. When it is more than 70% by weight, the conditioning effects may be decreased.

The hair care product of the present invention may be used in a shampoo, a rinse, a rinse in shampoo, a conditioning shampoo, a hair lotion, a hair conditioner, a hair treatment and a hair cream.

The hair care product of the present invention may contain other surface active agents, provided they do not eliminate the effects of the present invention. Examples thereof include an alkyl saccharide-type surface active agent, a polyoxyethylene alkyl ether-type surface active agent, a nonionic surface active agent such as a higher fatty acid alkanolamide or amine oxide, and a cationic surface active agent such as alkyltrimethylammonium chloride or N-acyl arginine lower alkyl ester pyrrolidone carboxylic acid salt.

A variety of ordinary additives can be used besides the above-mentioned surface active, provided they do not eliminate the effects of the present invention. Examples thereof include silicone polymers such as methylpolysiloxane, polyoxyethylene-methylpolysiloxane, polyoxypropylene-methylpolyoxysiloxane, poly(oxyethylene, oxypropylene) methylpolysiloxane, methylphenylpolysiloxane, fatty acid-modified polysiloxane, fatty acid alcohol-modified polysiloxane and amino acid-modified polysiloxane; wetting agents such as ethylene glycol, propylene glycol, 1,3-butylene glycol, glycerol and sorbitol; emulsifying agents such as glycerol monostearate and polyoxyethylene sorbitan monolaurate; hydrocarbons such as liquid paraffin, vaseline and squalene; esters such as isoproidyl myristate and octyldodecyl myristate; cellulose derivatives such as hydroxyethyl cellulose, hydroxypropyl cellulose and carboxymethyl cellulose; and anionic polymers such as acrylic acid-type polymers. Further, the hair care product of the present invention can contain antiseptics such as paraben derivatives, flavors, pigments, viscosity modifiers, pearling agents, antioxidants, disinfectants, anti-inflammatories, UV absorbers, pH adjustors and drugs.

Having generally described this invention, a further understanding can be obtained by reference to certain specific examples which are provided herein for purposes of illustration only and are not intended to be limiting unless otherwise specified.

EXAMPLES

Production Example 1

N-(2-hydroxy-3-dodecyloxypropyl)-L-arginine hydrochloride

L-arginine (17.4 g, 0.1 mmols) were dissolved in 100 ml of water in a three-necked round flask, and 100 ml of propanol were added thereto. Dodecyl glycidyl ether [made by Sakamoto Yakuhin Kogyo Co., Ltd., 24.2 g (0.1 mols)] was added thereto dropwise over a period of 30 minutes while being heat-stirred under reflux, and the mixture was stirred as such under reflux, for 3 hours. After it was identified through TLC and gas chromatography that dodecyl glycidyl ether disappeared, the residue was neutralized with 10.1 g (0.1 mols) of 36-% hydrochloric acid. The reaction solution was concentrated under reduced pressure, and the residue was purified through silica gel column chromatography (Kieselgel 60 made by Merck & Co., Inc., eluent—mixture of chloroform, methanol and acetic acid at a ratio of 3:1:0.5) to give 15.0 g of N-(2-hydroxy-3-dodecyloxypropyl)-L-arginine hydrochloride in a yield of 36.0%.

TLC (mixture of butanol, acetic acid and water at a ratio of 4:1:2): Rf=0.64; ESI mass spectrum: 417.5 (MH+); IR (NaCl, cm−1): 3177, 2955, 2920, 2853, 1692, 1628, 1468, 1397, 1377, 1215, 1116.

Production Example 2

N,N-bis(2-hydroxy-3-dodecyloxypropyl)-L-arginine hydrochloride

L-arginine (17.4 g, 0.1 mmols) was dissolved in 100 ml of water in a three-necked round flask, and 100 ml of i-propanol were added thereto. Dodecyl glycidyl ether (48.4 g, 0.2 mols) was added thereto dropwise over a period of 30 minutes while being heat-stirred under reflux, and the mixture was stirred as such under reflux for 3 hours. After it was identified through TLC and gas chromatography that dodecyl glycidyl ether disappeared, the residue was neutralized with 10.1 g (0.1 mols) of 36-% hydrochloric acid. The reaction solution was concentrated under reduced pressure, and the residue was purified through silica gel column chromatography (Kieselgel 60, eluent—mixture of chloroform, methanol and acetic acid at a ratio of 3:1:0.5) to give 11.4 g of N,N-bis (2-hydroxy-3-dodecyloxypropyl)-L-arginine hydrochloride in a yield of 17.2%.

TLC (mixture of butanol, acetic acid and water at a ratio of 4:1:2): Rf=0.72; ESI mass spectrum: 659.7 (MH+); IR (NaCl, cm−1): 3177, 2955, 2920, 2853, 1692, 1628, 1468, 1397, 1377,1215, 1120.

Production Example 3

N-(2-hydroxy-3-octadecyloxypropyl)-L-arginine hydrochloride

Production Example 1 was repeated using 17.4 g (0.1 mmols) of L-arginine and 32.6 g (0.1 of octadecylglycidyl ether (made by Sakamoto Yakuhin Kogyo K.K.) to give 21.2 g N-(2-hydroxy-3-octadecyloxypropyl)-L-arginine hydrochloride in a yield of 42.3%.

TLC (mixture of butanol, acetic acid and water at a ratio of 4:1:2): Rf=0.64; ESI mass spectrum: 501.5 (MH+); IR (NaCl, cm−1): 3175, 2955, 2917, 2851, 1692, 1628, 1468, 1377, 1215, 1121.

Production Example 4

N-ε-(2-hydroxy-3-dodecyloxypropyl)-L-lysine hydrochloride

L-lysine hydrochloride (18.3 g, 0.1 mmols) and 2.0 g (0.2 mols) of sodium hydroxide were dissolved in 100 ml of water in a three-necked round flask, and 100 ml of propanol were added thereto. Dodecyl glycidyl ether (24.2 g, 0.1 mols) was added thereto dropwise over a period of 30 minutes while being heat-stirred under reflux, and the mixture was stirred as such under reflux for 3 hours. After it was identified through TLC and gas chromatography that dodecyl glycidyl ether disappeared, the residue was neutralized with 10.1 g (0.1 mols) of hydrochloric acid. The reaction solution was concentrated under reduced pressure, and the residue was purified through silica gel—column chromatography (Kieselgel 60, eluent—mixture of chloroform, methanol and acetic acid at a ratio of 3:1:0.5) to give 10.1 g of N-ε-(2-hydroxy-3-dodecyloxypropyl)-L-lysine hydrochloride in a yield of 23.7%.

TLC (mixture of butanol, acetic acid and water at a ratio of 4:1:2): Rf=0.42; ESI mass spectrum: 389.4 (MH+); IR, (NaCl, cm-1): 2955, 2923, 2853, 1620, 1586, 1468, 1120.

Production Example 5

N-ε-(2-hydroxy-3-octadecyloxypropyl)-L-lysine hydrochloride

Production Example 4 was repeated using 18.3 g (0.1 mols) of L-lysine hydrochloride and 32.6 g (0.1 mols) of octadecyl glycidyl ether to give 12.0 g of N-ε-(2-hydroxy-3-octadecyloxypropyl)-L-lysine hydrochloride in a yield of 23.6%.

TLC (mixture of butanol, acetic acid and water at a ratio of 4:1:2): Rf=0.42; ESI mass spectrum: 473.5 (MH+); IR (NaCl, cm-1): 2955, 2923, 2853, 1620, 1586, 1468, 1120.

Production Example 6

Adduct of octadecyl glycidyl ether and L-lysine at a ratio of 2:1

L-lysine hydrochloride (18.3 g, 0.1 mols) and 2.0 g (0.2 mols) of sodium hydroxide were dissolved in 100 ml of water in a three-necked round flask, and 100 ml of i-propanol were added thereto. Then, 65.2 g (0.2 mols) of octadecylglycidyl ether were added dropwise thereto over a period of 30 minutes while being heat-refluxed and stirred. Further, the mixture was stirred under reflux for 3 hours. It was identified through TLC and gas chromatography that octadecylglycidyl ether disappeared. Thereafter, the resulting mixture was neutralized with 10.1 g (0.1 mols) of 36-% hydrochloric acid. The reaction solution was concentrated under reduced pressure, and the residue was purified through silica-gel column chromatography (Kieselgel 60, eluent= mixture of chloroform, methanol and acetic acid at a ratio of 3:1:0.5) to give 40.3 g of hydrochloride of an adduct of octadecylglycidyl ether and L-lysine at a ratio of 2:1 (yield 48.3).

ESI mass spectrum 799.7 (MH+); IR (NaCl, cm$^{-1}$): 2955, 2923, 2853, 1619, 1574, 1468, 1410, 1122.

Production Example 7

L-arginine was reacted with dodecylglycidyl ether in the same manner as in Production Example 1. After it was identified through TLC and gas chromatography that dodecylglycidyl ether disappeared, the reaction solution was neutralized with 36-% hydrochloric acid. The reaction solution was concentrated under reduced pressure to give 47.3 g of a reaction mixture.

Production Example 8

L-arginine (17.4 g, 0.1 mmols) was dissolved in 100 ml of water in a three-necked round flask, and 100 ml of i-propanol were added thereto. Heroxy 8 [made by ACI Japan Ltd., 25.6 g (0.1 mols)] was added thereto dropwise over a period of 30 minutes while being heat-stirred under reflux, and the mixture was stirred as such under reflux for 3 hours. After it was identified through TLC and gas chromatography that glycidyl ether disappeared, 12.9 g (0.1 mols) of DL-pyrrolidonecarboxyl acid. After i-propyl alcohol was distilled off under reduced pressure, the reaction solution was added to cold acetone to give 50.9 g of a mixture of N-(2-hydroxy-3-dodecyloxy)propyl-L-arginine-DL-pyrrolidone carboxylate and N-(2-hydroxy-3-tetradecyloxy)propyl-L-arginine-DL-pyrrolidone carboxylate.

ESI mass spectrum: 417.5 (MH+), 445.5 (MH+).

Production Example 9

N-(2-hydroxydodecyl)-L-arginine hydrochloride

Production Example 1 was repeated using 17.4 g (0.1 mols) of L-arginine and 18.4 g (0.1 mols) of 1,2-epoxydodecane to give 13.0 g of N-(2-hydroxydodecyl)-L-arginine hydrochloride in a yield of 32.9%.

Production Example 10

N-ε-(2-hydroxydodecyl)-L-lysine hydrochloride

Production Example 4 was repeated using 18.3 g (0.1 mols) of L-lysine hydrochloride and 18.4 g (0.1 mols) 1,2-epoxydodecane to give 7.0 g of N-ε-(2-hydroxydodecyl)-L-lysine hydrochloride in a yield of 19.2%.

Production Example 11

N-(2-hydroxyoctadecyl)-L-arginine hydrochloride

Production Example 1 was repeated using 17.4 g (0.1 mols) of L-arginine and 24.5 g (0.1 mols) of 1,2-epoxyoctadecane to give 16.8 g of N-(2-hydroxyoctadecyl)-L-arginine hydrochloride in a yield of 36.8%.

Test Example 1

Hair care products having compositions (unit-% by weight, total amount-100%) shown in Tables 2 to 7 below were prepared. Eight expert panelists washed the hair with a commercially available shampoo, and then used the hair care products. The organoleptic evaluation was conducted with respect to (a) a softness, (b) a combing property, (c) a moist feeling, (d) a stickiness of the hair after drying the same and (e) a feeling in coating. The results of the evaluation are shown in each Table. In the evaluation, average values were calculated according to the following standards shown in Table 1. The average value of 4.5 or more was evaluated as excellent (◎), that from 3.5 to 4.4 as good (0), that from 2.5 to 3.4 as common (Δ), and that from 2.4 or less as bad (x), respectively.

TABLE 1

Evaluation standard:

Softness of the hair:

5: very soft and smooth
4: soft
3: average
2: slightly hard
1: hard

Combing property:

5: very good with a high smoothness
4: good
3: average
2: slightly bad
1: bad (combing is sometimes interrupted)

TABLE 1-continued

Evaluation standard:

Moist feeling:

5: very good
4: good
3: average
2: slightly dry and hard
1: very dry and hard

Stickiness:

5: not sticky
4: little sticky
3: average
2: slightly sticky
1: sticky

Feeling in coating:

5: quite smooth feeling
4: smooth feeling
3: average
2: little smooth feeling
1: lack of a smooth feeling

TABLE 2

|  | Examples |  |  |  |  |  |  | Comparative Examples |  |  |  |  |  |  |
|---|---|---|---|---|---|---|---|---|---|---|---|---|---|---|
| Compound in Production Example 8 | 3.0 |  |  |  |  |  |  | 3.0 |  |  |  |  |  |  |
| Compound in Production Example 4 |  | 3.0 |  |  |  |  |  |  | 3.0 |  |  |  |  |  |
| Compound in Production Example 9 |  |  | 3.0 |  |  |  |  |  |  | 3.0 |  |  |  |  |
| Compound in Production Example 10 |  |  |  | 3.0 |  |  |  |  |  |  | 3.0 |  |  |  |
| Trimethylstearylammonium chloride |  |  |  |  | 3.0 |  |  |  |  |  |  | 3.0 |  |  |
| Dimethyldistearylammonium chloride |  |  |  |  |  | 3.0 |  |  |  |  |  |  | 3.0 |  |
| N α-cocoyl-L-arginine ethyl ester PCA salt |  |  |  |  |  |  | 3.0 |  |  |  |  |  |  | 3.0 |
| Cethl alcohol | 5.0 | 5.0 | 5.0 | 5.0 | 5.0 | 5.0 | 5.0 | 5.0 | 5.0 | 5.0 | 5.0 | 5.0 | 5.0 | 5.0 |
| Propylene glycol | 1.0 | 1.0 | 1.0 | 1.0 | 1.0 | 1.0 | 1.0 | 1.0 | 1.0 | 1.0 | 1.0 | 1.0 | 1.0 | 1.0 |
| Purified water | * | * | * | * | * | * | * | * | * | * | * | * | * | * |
| Softness | ⊚ | ⊚ | ⊚ | ○ | ⊚ | ○ | Δ | ○ | ○ | ○ | Δ | ○ | Δ | x |
| Combing property | ⊚ | ⊚ | ○ | ○ | ○ | ○ | Δ | ○ | ○ | Δ | Δ | Δ | Δ | x |
| Moist feeling | ⊚ | ○ | ⊚ | ⊚ | Δ | ○ | ⊚ | Δ | ○ | ○ | ○ | x | Δ | Δ |
| Stickiness | ○ | ○ | ○ | ○ | ○ | Δ | x | Δ | Δ | Δ | Δ | Δ | Δ | x |
| Feeling in coating | ⊚ | ○ | ⊚ | ⊚ | ○ | ○ | Δ | x | x | x | x | x | x | x |

*balance
PCA: pyrrolidonecarboxylic acid

TABLE 3

|  | Examples |  |  |  |  |  |  |  |  |  |  |  |  |
|---|---|---|---|---|---|---|---|---|---|---|---|---|---|
| Compound in Production Example 8 | 3.0 | 3.0 | 3.0 |  |  | 5.0 | 1.0 |  |  |  |  |  |  |
| Compound in Production Example 9 |  |  |  | 3.0 | 3.0 | 3.0 |  | 5.0 | 1.0 |  |  |  |  |
| Trimethylstearylammonium chloride |  |  |  |  |  |  |  |  |  |  | 3.0 | 3.0 | 3.0 |
| Stearyl alcohol | 5.0 |  |  | 5.0 |  |  | 3.0 | 10.0 |  | 5.0 |  |  |  |
| Myristyl alcohol |  | 5.0 |  |  | 5.0 |  |  |  | 10.0 | 1.5 | 10.0 |  | 5.0 |
| Behenyl alcohol |  |  | 5.0 |  |  | 5.0 |  |  |  | 1.5 | 10.0 |  | 5.0 |
| Glycerol | 1.0 | 1.0 | 1.0 | 1.0 | 1.0 | 1.0 | 1.0 | 1.0 | 1.0 | 1.0 | 1.0 | 1.0 | 1.0 |
| Purified water | * | * | * | * | * | * | * | * | * | * | * | * | * |
| Softness | ⊚ | ○ | ⊚ | ○ | ○ | ⊚ | ○ | ○ | ⊚ | ○ | ○ | ○ | ○ |
| Combing property | ○ | ⊚ | ○ | ○ | ⊚ | ○ | ○ | ○ | ○ | ○ | ○ | ○ | ○ |
| Moist feeling | ⊚ | ⊚ | ⊚ | ⊚ | ⊚ | ⊚ | ⊚ | ⊚ | ⊚ | ⊚ | Δ | Δ | Δ |
| Stickiness | ⊚ | ⊚ | ○ | ○ | ○ | ○ | ⊚ | ○ | ○ | ○ | ○ | Δ | x |
| Feeling in coating | ⊚ | ⊚ | ⊚ | ⊚ | ⊚ | ⊚ | ⊚ | ⊚ | ⊚ | ⊚ | Δ | Δ | Δ |

*balance

TABLE 4

|  | Examples |  |  |
|---|---|---|---|
| Compound in Production Example 2 | 3.0 |  |  |
| Compound in Production Example 6 |  | 3.0 |  |
| Compound in Production Example 7 |  |  | 3.0 |
| Cetyl alcohol | 5.0 | 5.0 | 5.0 |
| Glycerol | 1.0 | 1.0 | 1.0 |
| Purified water | * | * | * |
| Softness | ○ | ○ | ○ |
| Combing property | ⊚ | ○ | ⊚ |
| Moist feeling | ○ | ○ | ○ |
| Stickiness | ○ | ○ | ○ |
| Feeling in coating | ⊚ | ⊚ | ⊚ |

*balance

TABLE 5

|  | Examples |  |  |  |  |  |  |  | Comparative Examples |  |  |
|---|---|---|---|---|---|---|---|---|---|---|---|
| Compound in Production Example 3 | 3.0 | 3.0 | 3.0 | 3.0 | 1.0 |  |  |  |  |  |  |
| Compound in Production Example 11 |  |  |  |  |  | 3.0 | 3.0 | 3.0 |  |  |  |
| Trimethylstearylammonium chloride |  |  |  |  |  |  |  |  | 3.0 | 3.0 | 3.0 |
| Cationic polymer A | 1.0 |  |  | 0.3 | 3.0 | 1.0 |  |  | 1.0 |  |  |
| Cationic polymer B |  | 1.0 |  |  |  |  | 1.0 |  |  | 1.0 |  |
| Cationic polymer C |  |  | 5.0 |  |  |  |  | 1.0 |  |  | 1.0 |
| Cetyl alcohol | 2.0 | 2.0 | 2.0 | 2.0 | 2.0 | 2.0 | 2.0 | 2.0 | 2.0 | 2.0 | 2.0 |
| Propylene glycol | 3.0 | 3.0 | 3.0 | 3.0 | 3.0 | 3.0 | 3.0 | 3.0 | 3.0 | 3.0 | 3.0 |
| Glycerol | 2.0 | 2.0 | 2.0 | 2.0 | 2.0 | 2.0 | 2.0 | 2.0 | 2.0 | 2.0 | 2.0 |
| Purified water | * | * | * | * | * | * | * | * | * | * | * |
| Softness | ⊚ | ⊚ | ⊚ | ⊚ | ○ | ⊚ | ⊚ | ⊚ | ○ | Δ | Δ |
| Combing property | ○ | ○ | ⊚ | ○ | ○ | ○ | ○ | ○ | Δ | Δ | Δ |
| Moist feeling | ⊚ | ⊚ | ⊚ | ⊚ | ⊚ | ⊚ | ⊚ | ⊚ | ○ | ○ | ○ |
| Stickiness | ○ | ○ | ○ | ○ | ○ | ○ | ○ | ○ | ○ | ○ | ○ |

Cationic polymer A: "polymerJR-400" made by Union Carbide Japan K.K.
Cationic polymer B: "polymerJR-30M" made by Union Carbide Japan K.K.
Cationic polymer C: "Merquat550" made by Calgon Corporation
*balance

TABLE 6

|  | Examples |  |  |  |  |  |  |  |  |  | Comparative Examples |  |  |  |  |
|---|---|---|---|---|---|---|---|---|---|---|---|---|---|---|---|
| Compound in Production Example 1 | 6.0 | 1.0 | 1.0 | 3.0 | 1.0 |  |  |  |  |  |  |  |  |  |  |
| Compound in Production Example 11 |  |  |  |  |  | 4.0 | 4.0 | 4.0 | 4.0 | 4.0 |  |  |  |  |  |
| Trimethylstearylammonium chloride |  |  |  |  |  |  |  |  |  |  | 4.0 | 4.0 | 4.0 | 4.0 | 4.0 |
| Amidobetaine-type ampholytic surface active agent (*1) | 0.2 |  |  |  |  | 3.0 |  |  |  |  | 3.0 |  |  |  |  |
| Imidazoline-type ampholytic surface active agent (*2) |  | 0.5 |  |  |  |  | 3.0 |  |  |  |  | 3.0 |  |  |  |
| Stearyl dihydroxyethyl amino acetic acid betaine |  |  | 2.0 |  |  |  |  | 3.0 |  |  |  |  | 3.0 |  |  |
| Laurylhydroxysulfobetaine |  |  |  | 2.0 |  |  |  |  | 3.0 |  |  |  |  | 3.0 |  |
| Laurylphosphobetaine |  |  |  |  | 10.0 |  |  |  |  | 3.0 |  |  |  |  | 3.0 |
| Cetyl alcohol | 3.0 | 3.0 | 3.0 | 3.0 | 3.0 | 3.0 | 3.0 | 3.0 | 3.0 | 3.0 | 3.0 | 3.0 | 3.0 | 3.0 | 3.0 |
| Propylene glycol | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Purified water | * | * | * | * | * | * | * | * | * | * | * | * | * | * | * |
| Softness | ⊚ | ○ | ○ | ⊚ | ○ | ⊚ | ⊚ | ⊚ | ⊚ | ⊚ | ○ | ○ | Δ | Δ | ○ |
| Combing property | ⊚ | ○ | ○ | ⊚ | ○ | ⊚ | ⊚ | ○ | ○ | ○ | ○ | Δ | ○ | Δ | ○ |
| Moist feeling | ○ | ○ | ⊚ | ○ | ⊚ | ○ | ○ | ○ | ○ | ○ | Δ | Δ | Δ | ○ | Δ |
| Stickiness | ○ | ⊚ | ⊚ | ○ | ⊚ | ○ | ○ | ○ | ○ | ○ | Δ | Δ | Δ | ○ | ○ |

(*1) "ANON BF" made by NOF Corporation
(2) "Softazoline CH" made by Kawaken Fine Chemicals Co., Ltd.
*balance

TABLE 7

|  | Examples |  |  |  |  |  |  |  |  |  | Comparative Examples |  |  |  |  |
|---|---|---|---|---|---|---|---|---|---|---|---|---|---|---|---|
| Compound in Production Example 8 | 1.0 | 5.0 | 10.0 | 4.0 | 4.0 | 4.0 | 4.0 | 4.0 | 4.0 | 4.0 |  |  |  |  |  |
| N α-cocoyl-L-arginine ethyl ester PCA salt |  |  |  |  |  |  |  |  |  |  | 1.0 | 10.0 | 4.0 | 4.0 | 4.0 |
| Cocoyl glutamic acid TEA salt | 10.0 |  |  |  |  |  |  |  |  |  | 10.0 |  |  |  |  |
| Lauroyl sarcosine TEA salt |  | 10.0 |  |  |  |  |  |  |  |  |  |  |  |  |  |
| Lauroyl metyl laurine sodium salt |  |  | 10.0 |  |  |  |  |  |  |  |  | 10.0 |  |  |  |
| Polyoxyethylene lauryl ether acetic acid sodium salt |  |  |  | 5.0 |  |  |  |  |  |  |  |  |  |  |  |
| Cocoyl isethionic acid sodium salt |  |  |  |  | 5.0 |  |  |  |  |  |  |  | 5.0 |  |  |
| Sulfosuccinic acid lauryl di-sodium salt |  |  |  |  |  | 5.0 |  |  |  |  |  |  |  |  |  |
| Polyoxyethlene sulfosuccinic acid lauryl di-sodium salt |  |  |  |  |  |  | 5.0 |  |  |  |  |  |  | 5.0 |  |
| Lauryl sulfonic acid TEA salt |  |  |  |  |  |  |  | 5.0 |  |  |  |  |  |  |  |
| Polyoxyethylene lauryl ether sulfonic acid TEA salt |  |  |  |  |  |  |  |  | 30.0 |  |  |  |  |  | 30.0 |
| α-Olefin sulfonic acid sodium salt |  |  |  |  |  |  |  |  |  | 0.5 |  |  |  |  |  |
| Cetyl alcohol | 10.0 | 3.0 | 10.0 | 3.0 | 3.0 | 3.0 | 3.0 | 3.0 | 3.0 | 3.0 | 10.0 | 10.0 | 3.0 | 3.0 | 3.0 |
| Propylene glycol | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| Purified water | * | * | * | * | * | * | * | * | * | * | * | * | * | * | * |
| Softness | ○ | ○ | ○ | ○ | ○ | ○ | ⊚ | ○ | ○ | ○ | x | Δ | x | Δ | Δ |
| Combing property | ○ | ⊚ | ⊚ | ⊚ | ○ | ○ | ○ | ○ | ○ | ○ | x | x | x | x | x |

TABLE 7-continued

|  | Examples |  |  |  |  |  |  |  |  |  | Comparative Examples |  |  |  |  |
|---|---|---|---|---|---|---|---|---|---|---|---|---|---|---|---|
| Moist feeling | ◎ | ○ | ◎ | ◎ | ○ | ◎ | ◎ | ○ | ○ | ◎ | x | x | x | x | x |
| Stickiness | ◎ | ○ | ○ | ○ | ○ | ○ | ○ | ◎ | ◎ | ◎ | x | x | Δ | x | x |

TEA: Triethanolamine
*balance

Reference Example 1

Irrigation test of the skin and the eye mucous membrane

The primary irrigations of the skin and the eye mucous membrane were measured by the following test methods.

(1) Test for Skin Primary Irritation

Each of four New Zealand white male rabbits was seal-coated with a patch test plaster impregnated with 0.3 ml of a 1-% test compound aqueous solution for 24 hours. The plaster was then removed from the rabbit. After 24 hours, the irritation was evaluated according to the Draise's evaluation standard shown in Table 8.

TABLE 8

| Draise's evaluation score | Irritation level |
|---|---|
| 4 or more | heavy |
| from 2 to less than 4 | light |
| less than 2 | slight |

(2) Test for Eye Mucous Membrane Primary Irritation

The lower eyelids of both eyes of each of four New Zealand white male rabbits were formed into a pouch, and 0.1 ml of a 1-% surface active agent aqueous solution were dropped therein. Thereafter, the upper and lower eyelids were gently joined. After 24 hours of the dropping, the irritation was evaluated according to the Draise's evaluation standard shown in Table 9.

TABLE 9

| Draise's evaluation score | Irritation level |
|---|---|
| 50 or more | heavy |
| from 20 to less than 50 | medium |
| from 10 to less than 20 | light |
| less than 10 | slight |

The results of the above two tests are shown in Table 10.

TABLE 10

| Compound | Skin irritation | Mucous membrane irritation |
|---|---|---|
| Compound in Production Example 8 | slight | slight |
| Compound in Production Example 4 | slight | slight |
| Compound in Production Example 9 | slight | slight |
| Trimethylstearyl ammonium chloride | heavy | medium |
| Nα-cocoyl-L-arginine ethyl ester salt | slight | slight |

Reference Example 2

Test for compatibility with an anionic surface active agent

Ten milliliters of a 1-% aqueous solution of each of polyoxyethylene lauryl ether sulfonic acid sodium salt (LES) and sodium dodecyl sulfate (SDS) which are anionic surface active agents were prepared. To this were gradually added 10 ml of a 1-% aqueous solution of each surface active agent shown in Table 11 at 25° C. The point at which the solution turned blue and the point at which the solution turned milk-white were visually observed. The results of the evaluation are shown in Table 11.

TABLE 11

|  | LES | | SDS | |
|---|---|---|---|---|
|  | Blue point | Milk-white point | Blue point | Milk-white point |
| Compound in Production Example 8 | 5 ml | 10 ml | 7 ml | * |
| Compound in Production Example 9 | 5 ml | 10 ml | 5 ml | * |
| Monostearyl ammonium chloride | 5 ml | 8 ml | 1 ml | 3 ml |

Reference Example 3

Test for Biodegradability

A test for biodegradability was conducted for 28 days according to the OECD chemical product test Guideline 301C corrected MITI test (I)—1981, incorporated herein by reference. In the test, an active sludge in a sewage disposal plant was used as a microorganism source, and biochemical oxygen demand (BOD) was continuously measured using a sealed biochemical oxygen demand automatic measuring device (BOD measuring device).

(a) BOD biodegradability:

The biodegradability of the specimen is shown in Table 12. The biodegradability of aniline in a standard test lot was 40% or more for 7 days. Thus, this test was verified.

TABLE 12

| The results of BOD biodegradability measurement (%) | | | | |
|---|---|---|---|---|
| Test lot | Day 7 | Day 14 | Day 21 | Day 28 |
| Compound in Production Example 1 | | | | |
| Culture test lot 1 | 16.1 | 40.1 | 55.0 | 60.0 |
| Culture test lot 2 | 18.4 | 38.1 | 57.2 | 67.3 |
| Culture test lot 3 | 16.1 | 42.6 | 55.6 | 57.2 |
| Average value | 16.9 | 40.4 | 55.0 | 60.0 |

TABLE 12-continued

The results of BOD biodegradability measurement (%)

| Test lot | Day 7 | Day 14 | Day 21 | Day 28 |
|---|---|---|---|---|
| Monostearylarammonium chloride | | | | |
| Culture test lot 1 | 0 | 0 | 0 | 0 |
| Culture test lot 2 | 0 | 0 | 0 | 0 |
| culture test lot 3 | 0 | 0 | 0 | 0 |
| Average value | 0 | 0 | 0 | 0 |
| Non-culture test lot | <5 | 10.2 | 11.8 | 12.4 |
| Aniline | | | | |
| Standard test lot | 65.4 | 72.4 | 75.7 | 77.7 |

Formulation Example 1

Hair Treatment

A hair treatment was prepared from the starting materials shown in Table 13. That is, A and B components (excluding the flavor) were dissolved separately at from 80 to 85° C. while being stirred. Then, the B components dissolved were added to the A components dissolved. The mixture was cooled to 50° C. while being stirred using a mono-mixer. The flavor was added thereto, and the mixture was cooled to 30° C. while being stirred to obtain the product.

TABLE 13

| A components: | |
|---|---|
| Cetyl alcohol (*1) | 5.0 wt. % |
| Liquid paraffin | 5.0 |
| N-lauroyl-L-glutamic acid POE (2) stearyl ether (*2) | 1.5 |
| "Amifat P-30" (*3) | 2.5 |
| POE (30) hardened castor oil triisostearate (*4) | 1.5 |
| Saturated fatty acid glyceride (FW680) (*5) | 3.0 |
| POE (25) monostearate (*6) | 1.0 |
| Dimethylsiloxane-aminopropylsiloxane copolymer (40%) (*7) | 1.0 |
| B components: | |
| Compound in Production Example 1 | 1.0 |
| Monostearyltrimethylammonium chloride (50%) (*8) | 0.4 |
| Butylene glycol | 5.0 |
| Dimethylstearylamine oxide (35%) (*9) | 1.0 |
| "Prodew 100" (*10) | 2.0 |
| Antiseptic | suitable amount |
| Purified water | balance |
| Flavor | suitable amount |
| Total | 100% |

POE: polyoxyethylene
(*1) "Kalcol 68' made by Kao Corporation.
(*2) "Amitel LGS-2" made by Nippon Emulsion Co., Ltd.
(*3) Pyroglutamic acid oleic acid glyceryl made by Ajinomoto Co., Inc.
(*4) Emalex RWIS-330" made by Nippon Emulsion Co., Ltd.
(*5) "Witepsol H-15" made by Mitsuba Trading Co., Ltd.
(*6) "Nikkol MYS-25" made by Nikko Chemicals Co., Ltd.
(*7) "SM8702C(40%)" made by Dow Corning Toray Silicone Co., Ltd.
(*8) "Arquad T-800 (50%)" made by Lion Corporation.
(*9) "Unisafe A-SM (35)" made by NOF Corporation.
(*10) Trade name for mixture of DL-pyrrolidone carboxylic acid sodium salt, L-proline, sodium lactate, sorbitol and hydrolyzed collagen made by Ajinomoto Inc.

Formulation Example 2

Hair Treatment

A hair treatment was prepared from the starting materials shown in Table 14. That is, A and B components (excluding the flavor) were dissolved separately at from 80 to 85° C. while being stirred. Then, the B components dissolved were added to the A components dissolved. The mixture was cooled to 50° C. while being stirred using a monomixer. The flavor was added thereto, and the mixture was cooled to 30° C. while being stirred to obtain the product.

TABLE 14

| A components: | |
|---|---|
| Behenyl alcohol | 8.0 wt. % |
| Liquid paraffin | 3.0 |
| PEG (20) sorbitan monostearate (*1) | 1.0 |
| Dioctyldodecyl N-lauroyl-L-glutamate (*2) | 2.0 |
| "Amifat P-30" | 2.0 |
| Glyceryl monostearate (*3) | 2.0 |
| POE (25) glyceryl monopyroglutamate (*4) | 2.0 |
| Vitamin E | 0.2 |
| B components: | |
| Compound in Production Example 4 | 1.0 |
| Glycerol | 5.0 |
| Phenoxyethanol | 3.0 |
| 1, 3-butylene glycol | 1.0 |
| "Prodew 100" | 4.0 |
| Purified water | balance |
| Flavor | suitable amount |
| Total | 100% |

(*1) "Nikkol TS-10" made by Nikko Chemicals Co.., Ltd.
(*2) "Amiter LGOD" made by Nippon Emulsion Co., Ltd.
(*3) "Emalex GMS-45RT" made by Nippon Emulsion Co., Ltd.
(*4) "Pyroter GPI-25" made by Nippon Emulsion Co., Ltd.
PEG: polyethylene glycol

Formulation Example 3

Hair Treatment

A hair treatment was prepared from the starting materials shown in Table 15. That is, A and B components (excluding the flavor) were dissolved separately at from 80 to 85° C. while being stirred. Then, the B components dissolved were added to the A components dissolved. The mixture was cooled to 30° C. while being stirred using a monomixer. The flavor was added thereto, and the mixture was cooled to 30° C. while being stirred to obtain the product.

TABLE 15

| A components: | |
|---|---|
| Cetostearyl alcohol (*1) | 9.0 wt. % |
| N-lauroyl-L-glutamic acid POE (2) octadecyl ether diester (*2) | 1.0 |
| Octyl dodecanol | 1.0 |
| "Eldew CL-301" (*3) | 1.0 |
| Glyceryl monostearate | 1.0 |
| POE (40) monostearate (*4) | 1.0 |
| Ethylene glycol distearate (*5) | 1.0 |
| B components: | |
| Compound in Production Example 1 | 1.0 |
| Dimethylstearylamine oxide (35%) (*6) | 1.0 |
| N-[2-hydroxy-3-(trimethylammonio)propyl] chloride collagen hydrolyzate (*7) | 2.0 |

TABLE 15-continued

| | |
|---|---|
| "Prodew 100" | 1.0 |
| 1,3-butylene glycol | 5.0 |
| Purified water | balance |
| Antiseptic | suitable amount |
| Flavor | suitable amount |
| Silicone emulsion (*8) | 1.0 |
| Total | 100.0% |

(*1) "Kalcol 6850" made by Kao Corporation
(*2) "Amiter LGOD-2(H)" made by Nippon Emulsion Co., Ltd.
(*3) Lauroyl-L-glutamic acid (cholesteryl, behenyl, octyldodecyl) made by Ajinomoto Co., Inc.
(*4) "Emalex 840" made by Nippon Emulsion Co., Ltd.
(*5) "Emalex EG-di-S" made by Nippon Emulsion Co., Ltd.
(*6) "Unisafe A-SM (35%)" made by NOF Corporation
(*7) "Promois W-52Q" made by Seiwa Kasei Co., Ltd.
(*8) "BY-22-034" made by Dow Corning Toray Silicone Co., Ltd.

Formulation Example 4 (hair treatment)

A hair treatment was prepared using a formulation shown in The following Table 16.

TABLE 16

| | |
|---|---|
| Compound in Production Example 1 | 2.5 wt. % |
| Liquid paraffin | 3.0 |
| Cetanol/stearyl alcohol mixture (3:7) | 3.5 |
| Sorbitan monostearate | 0.3 |
| Sorbitan distearate | 0.6 |
| Glycerol distearate | 1.5 |
| POE (n = 20) nonylphenyl ether | 0.7 |
| Coconut oil fatty acid polypeptide | 0.3 |
| Isostearic acid | 0.2 |
| Glycerol | 10.0 |
| Flavor | 0.3 |
| Purified water | balance |
| Total | 100.0% |

Formulation Example 5 (hair treatment)

A hair treatment was prepared using a formulation shown in the following Table 17.

TABLE 17

| | |
|---|---|
| Compound in Production Example 5 | 2.0 wt. % |
| DL-$\alpha$-tocopherol acetate | 0.01 |
| $\beta$-Carotene | 0.005 |
| Liquid paraffin | 3.0 |
| Cetanol/stearyl alcohol mixture (3:7) | 3.5 |
| Stearic acid | 0.5 |
| Isopropyl palmitate | 1.0 |
| Sorbitan monopalmitate | 1.0 |
| Glycerol monostearate | 1.0 |
| POE (10 mols) stearyl ether | 0.5 |
| N-laurylglutamic acid-2-octyldodecyl ether diester | 0.1 |
| Glycerol | 10.0 |
| Methyl paraben | 0.1 |
| Flavor | 0.3 |
| Purified water | balance |
| Total | 100.0% |

Formulation Example 6 (hair treatment)

A hair treatment was prepared using a formulation shown in the following Table 18.

TABLE 18

| | |
|---|---|
| Compound in Production Example 4 | 1.5 wt. % |
| N-cocoyl glutamic acid TEA salt | 1.0 |
| Stearyl alcohol | 3.0 |
| Collagen hydrolyzate | 0.5 |
| Stearyl ether ethylene oxide adduct (ethylene oxide addition number 5) | 0.3 |
| Soybean Lecithin | 0.5 |
| Propylene glycol | 5.0 |
| Methyl paraben | 0.1 |
| Flavor | 0.5 |
| Purified water | balance |
| Total | 100.0% |

Formulation Example 7 (hair treatment)

Three types of hair treatment were prepared using a formulation shown in the following Table 19.

TABLE 19

| | Hair treatment | | |
|---|---|---|---|
| | a (wt. %) | b (wt. %) | c (wt. %) |
| Compound in Production Example 1 | 1.0 | 1.0 | 1.0 |
| Stearyltrimethylammonium chloride | 0.5 | 0.5 | 0.5 |
| Squalene | 1.0 | 1.0 | 1.0 |
| Vaseline | 1.0 | 1.0 | 1.0 |
| Beeswax | 0.5 | 0.5 | 0.5 |
| Sorbitan monooleic acid ester | 1.0 | 1.0 | 1.0 |
| Cetyl alcohol/stearyl alcohol mixture (3:7) | 5.0 | 5.0 | 5.0 |
| Hydroxymethyl cellulose | 0.5 | — | — |
| Cationic cellulose | — | 1.0 | — |
| Acyl peptide (MW = 400) | — | — | 1.0 |
| Polyoxyethylene hardened castor oil triisostearate | 1.0 | 1.0 | 1.0 |
| Methyl p-oxybenzoate | 0.2 | 0.2 | 0.2 |
| Propyl p-oxybenzoate | 0.1 | 0.1 | 0.1 |
| Flavor | 0.3 | 0.3 | 0.3 |
| Purified water | balance | balance | balance |
| Total | 100.0% | 100.0% | 100.0% |

Formulation Example 8 (hair treatment)

A hair treatment was prepared using a formulation shown in the following Table 20.

TABLE 20

| | |
|---|---|
| Compound in Production Example 3 | 1.0 wt. % |
| Dimethylsilicone | 0.5 |
| Liquid paraffin | 15.0 |
| Cetanol/stearyl alcohol mixture (3:7) | 3.5 |
| Stearic acid | 0.5 |
| Sorbitan monopalmitate | 1.5 |
| Polyoxyethylene (p = 15) stearyl ether | 0.7 |
| Propylene glycol | 5.0 |
| Purified water | balance |
| Total | 100.0% |

Formulation Example 9 (hair treatment)

A hair treatment was prepared using a formulation shown in the following Table 21.

TABLE 21

| | |
|---|---|
| Compound in Production Example 5 | 1.0 wt. % |
| Camellia oil | 3.0 |
| Liquid paraffin | 10.0 |
| Cetanol/stearyl alcohol mixture (1:9) | 3.5 |
| Stearic acid | 0.5 |
| Sorbitan monopalmitate | 1.5 |
| Polyoxyethylene (p = 15) stearyl ether | 0.7 |
| Propylene glycol | 10.0 |
| Purified water | balance |
| Total | 100.0% |

Formulation Example 10 (hair treatment)

A hair treatment was prepared using a formulation shown in the following Table 22.

TABLE 22

| | |
|---|---|
| Compound in Production Example 1 | 2.0 wt. % |
| Compound in Production Example 4 | 1.0 |
| Liquid paraffin | 3.0 |
| Cetanol/stearyl alcohol mixture (3:7) | 3.5 |
| Glycerol monolauryl ether | 0.5 |
| Isopropyl myristate | 1.0 |
| Sorbitan monopalmitate | 1.0 |
| Glycerol monostearate | 1.0 |
| P.O.E (n = 10) stearyl ether | 0.5 |
| N-lauroylglutamic acid 2-octyl-dodecyl ether diester | 1.0 |
| Glycerol | 10.0 |
| Methyl paraben | 0.1 |
| Flavor | 0.3 |
| Purified water | balance |
| Total | 100.0% |

Formulation Example 11

Hair Rinse

A hair treatment was prepared from the starting materials shown in Table 23. That is, A and B components (excluding the flavor) were dissolved separately at from 80 to 85° C. while being stirred. Then, the B components dissolved were added to the A components dissolved. The mixture was cooled to 30° C. while being stirred to obtain the product.

TABLE 23

| | |
|---|---|
| A components: | |
| N-lauroyl-L-glutamic acid POE (2) octadodecyl ether diester (*1) | 1.5 wt. % |
| Cetyl alcohol | 3.5 |
| "Amifat P-30" | 1.0 |
| B components: | |
| Compound in Production Example 1 | 0.8 |
| Dimethylstearylamine oxide (35%) (*2) | 1.0 |
| "Prodew 100" | 2.0 |
| Butylene glycol | 3.0 |
| Antiseptic | suitable amount |
| Purified water | balance |
| Total | 100.0% |

TABLE 23-continued (*1) "Amiter LGOD-2" made by Nippon Emulsifier Co., Ltd.
(*2) "Unisafe A-SM (35%)" made by NOF Corporation

Formulation Example 12 (hair raise)

A hair rinse was prepared using a formulation shown in the following Table 24.

TABLE 24

| | |
|---|---|
| Compound in Production Example 1 | 1.0 wt. % |
| Cationic polymer (*1) | 1.0 |
| Cetanol | 2.0 |
| Liquid paraffin | 1.0 |
| P.O.E. (5 mols) stearyl ether | 1.6 |
| Propylene glycol | 3.0 |
| Glycerol | 2.0 |
| Purified water | balance |
| Total | 100.0% |

(*1) "Polymer JR-400", made by Union Carbide Japan K.K.

Formulation Example 13 (hair cream)

A hair cream was prepared using a formulation shown in the following Table 25.

TABLE 25

| | |
|---|---|
| Compound in Production Example 1 | 1.0 wt. % |
| Stearic acid | 1.5 |
| cetanol/stearyl alcohol mixture (3:7) | 1.0 |
| L-proline | 1.5 |
| Glyceryl monostearate | 1.0 |
| Sorbitol | 5.0 |
| Polyoxyethylene (p = 15) cetyl ether | 2.0 |
| Hydroxyethyl cellulose | 0.5 |
| Flavor | trace |
| Pigment | trace |
| Purified water | balance |
| Total | 100.0% |

Formulation Example 14 (hair cream)

A hair cream was prepared using a formulation shown in the following Table 26.

TABLE 26

| | |
|---|---|
| Compound in Production Example 1 | 1.5 wt. % |
| Sodium N-myristoylmethyltaurine | 0.5 |
| Stearyl alcohol | 5.0 |
| Stearic acid | 1.0 |
| Sorbitan monostearate | 2.0 |
| Avocado oil | 1.5 |
| Soybean phospholipid | 0.8 |
| Propylene glycol | 7.0 |
| Flavor and pigment | suitable amounts |
| Purified water | balance |
| Total | 100.0% |

Formulation Example 15 (hair cream)

A hair cream was prepared using a formulation shown in the following Table 27.

TABLE 27

| | |
|---|---|
| Compound in Production Example 8 | 1.0 wt. % |
| Compound in Production Example 5 | 1.0 |
| Beeswax | 5.0 |
| Lanoline | 5.0 |
| Liquid paraffin | 5.0 |
| Isopropyl myristate | 3.0 |
| Cetanol/stearyl alcohol mixture (1:9) | 3.0 |
| Stearic acid | 5.0 |
| Sorbitan monostearate | 1.0 |
| Glyceryl monostearate | 1.0 |
| P.O.E. (n = 10) stearyl ether | 0.5 |
| P.O.E. (n = 30) hardened castor oil monoisostearate | 0.3 |
| Triethanolamine | 1.0 |
| Glycerol | 5.0 |
| Sorbitol | 2.0 |
| Methyl paraben | 0.1 |
| Flavor | 0.2 |
| Purified water | balance |
| Total | 100.0% |

Formulation Example 16 (hair lotion)

A hair lotion was prepared using a formulation shown in the following Table 28.

TABLE 28

| | |
|---|---|
| Compound in Production Example 1 | 1.0 wt. % |
| Squalene | 1.0 |
| Cetanol/stearyl alcohol mixture (1:9) | 1.5 |
| Glycerol monostearate | 0.5 |
| N-lauroylglutamic acid 2-octyldodecyl ether diester | 0.5 |
| Stearyltrimethylammonium chloride | 0.3 |
| Polyethylene glycol | 3.0 |
| 1, 3-butylene glycol | 5.0 |
| Methyl paraben | 0.1 |
| Purified water | balance |
| Total | 100.0% |

Formulation Example 17 (hair treatment)

Four types of hair treatments were prepared using a formulation shown in the following Table 29.

TABLE 29

| | Hair treatment | | | |
|---|---|---|---|---|
| | a wt. % | b wt. % | c wt. % | d wt. % |
| Compound in Production Example 5 | 1.0 | 1.0 | 1.0 | 1.0 |
| Benehyltrimethylammonium chloride | 1.0 | 1.0 | 1.0 | 1.0 |
| Squalane | 1.5 | 1.5 | 1.5 | 1.5 |
| Vaseline | 0.5 | 0.5 | 0.5 | 0.5 |
| Beeswax | 0.5 | 0.5 | 0.5 | 0.5 |
| Polyoxyethylene (P = 7) stearyl ether | 1.0 | 1.0 | 1.0 | 1.0 |
| Eicosan-2-ol (n = 20) | 3.0 | 3.0 | 3.0 | 3.0 |
| Cetyl alcohol/stearyl alcohol mixture (5:5) | 1.5 | 1.5 | 1.5 | 1.5 |
| Hydroxyethyl cellulose | 0.5 | — | — | — |
| Cationic cellulose | — | 0.5 | — | — |
| Acyl peptide (MW = 400) | — | — | 0.5 | — |
| Stearic acid | — | — | — | 0.5 |
| Butyl alcohol | 0.5 | 0.5 | 0.5 | 0.5 |
| Pigment | trace | trace | trace | trace |
| Flavor | trace | trace | trace | trace |
| Purified water | balance | balance | balance | balance |
| Total | 100% | 100% | 100% | 100% |

Formulation Example 18

Hair Treatment

A hair treatment was prepared from the starting materials shown in Table 30. That is, A and 3 components (excluding the flavor) were dissolved separately at from 80 to 85° C. while being stirred. Then, the B components dissolved were added to the A components dissolved. The mixture was cooled to 50° C. while being stirred using a monomixer. The flavor was added thereto, and the mixture was cooled to 30° C. while being stirred to obtain the product.

TABLE 30

| | |
|---|---|
| A components: | |
| Behenyl alcohol | 8.0 wt. % |
| Liquid paraffin | 3.0 |
| PEG (20) sorbitan monostearate | 1.0 |
| Dioctyldodecyl N-lauroyl-L-glutamate | 2.0 |
| "Amifat P-30" | 2.0 |
| Glyceryl monostearate | 2.0 |
| POE (25) glyceryl monopyroglutamate | 2.0 |
| Vitamin E | 0.2 |
| B components: | |
| Compound in Production Example 8 | 1.0 |
| Glycerol | 5.0 |
| 1, 3-butylene glycol | 1.0 |
| "Prodew 100" | 4.0 |
| Antiseptic | suitable amount |
| Purified water | balance |
| Flavor | suitable amount |
| Total | 100% |

Formulation Example 19 (hair treatment)

A hair treatment was prepared using a formulation shown in the following Table 31.

TABLE 31

| | |
|---|---|
| Compound in Production Example 8 | 4.5 wt. % |
| N-cocoyl glutamic acid TEA salt | 1.0 |
| Stearyl alcohol | 3.0 |
| Collagen hydrolyzate | 0.5 |
| Stearyl ether ethylene oxide adduct (ethylene oxide addition number 5) | 0.3 |
| Soybean lecithin | 0.5 |
| Propylene glycol | 5.0 |
| Methyl paraben | 0.1 |
| Flavor | 0.5 |
| Purified water | balance |
| Total | 100% |

Formulation Example 20

A hair rinse was prepared using a formulation shown in the following Table 32.

TABLE 32

| | |
|---|---|
| Compound in Production Example 8 | 3.0 wt. % |
| Cationic polymer (*1) | 1.0 |
| Cetanol | 2.0 |
| Liquid paraffin | 1.0 |
| POE (5) stearyl ether | 1.6 |
| Propylene glycol | 3.0 |
| Glycerol | 2.0 |
| purified water | balance |
| Total | 100% |

(*1) "Polymer JR-400" made by Union Carbide Japan K.K.

Formulation Example 21 (hair treatment)

A hair treatment was prepared using a formulation shown in the following Table 33.

TABLE 33

| | |
|---|---|
| Compound in Production Example 8 | 3.0 wt. % |
| dl-α-tocopherol acetate | 0.01 |
| β-Carotene | 0.005 |
| Liquid paraffin | 3.0 |
| Cetanol/stearyl alcohol mixture (7:3) | 3.5 |
| Stearic acid | 0.5 |
| Isopropyl palmitate | 1.0 |
| Sorbitan monopalmitate | 1.0 |
| Glycerol monostearate | 1.0 |
| POE (10) stearyl ether | 0.5 |
| N-laurylglutamic acid-2-octyldodecyl diester | 1.0 |
| Glycerol | 10.0 |
| Methyl paraben | 0.1 |
| Flavor | 0.3 |
| Purified water | balance |
| Total | 100% |

Formulation Example 22 (rinse in shampoo)

A rinse in shampoo was prepared using a formulation shown in the following Table 34.

TABLE 34

| | |
|---|---|
| Compound in Production Example 8 | 4.5 wt. % |
| N-coconut oil fatty acid acyl-N-carboxyethyl-N-hydroxyethyl ethylenediamine sodium salt | 16.0 |
| Coconut oil fatty acid diethanolamide | 4.0 |
| N-lauroyl-N-methyl-β-alanine sodium salt | 1.0 |
| Silicone derivative | 1.0 |
| Polyoxyethylenealkylpolyamine | 1.0 |
| Flavor, pigment and PH adjustor | suitable amounts |
| Purified water | balance |
| Total | 100% |

Formulation Example 23 (hair treatment)

A hair treatment was prepared using a formulation shown in the following Table 35.

TABLE 35

| | |
|---|---|
| Compound in Production Example 8 | 2.5 wt. % |
| Glyceryl monostearate | 1.0 |
| Triglyceride octanate | 3.0 |
| Cetanol | 2.0 |
| Dimethylpolysiloxane | 10.0 |
| Glycerol | 8.0 |
| Cationic cellulose | 0.1 |
| Methyl paraben | 0.3 |
| Purified water | balance |
| Total | 100% |

Formulation Example 24

Hair Treatment

A hair treatment was prepared from the starting materials shown in Table 36. That is, A and B components (excluding the flavor) were dissolved separately at from 80 to 85° C. while being stirred. Then, the B components dissolved were added to the A components dissolved. The mixture was cooled to 50° C. while being stirred using a monomixer. The flavor was added thereto, and the mixture was cooled to 30° C. while being stirred to obtain the product.

TABLE 36

| | |
|---|---|
| A components: | |
| Cetyl alcohol | 5.0 wt. % |
| Liquid paraffin | 5.0 |
| N-lauroyl-L-glutamic acid POE (2) stearyl ether | 1.5 |
| "Amifat P-30" (*1) | 2.5 |
| POE (30) hardened castor oil triisostearate | 1.5 |
| Saturated fatty acid glyceride (FW680) | 3.0 |
| POE (25) monostearate | 1.0 |
| Dimethylsiloxane-aminopropylsiloxane copolymer (40%) | 1.0 |
| B components: | |
| Compound in Production Example 8 | 3.0 |
| Monostearyltrimethylammonium chloride (50%) | 0.4 |
| Butylene glycol | 5.0 |
| Dimethylstearylamine oxide | 1.0 |
| "Prodew 100" | 2.0 |
| Antiseptic | suitable amount |
| Purified water | balance |
| Flavor | suitable amount |
| Total | 100% |

The hair care products shown in Formulation Examples 1 to 24 were all excellent in the conditioning effects and the sensory feeling during use.

Obviously, additional modifications and variations of the present invention are possible in light of the above teachings. It is therefore to be understood that within the scope of the appended claims, the invention may be practiced otherwise than as specifically described herein.

This application is based on Japanese Application No. 246885/1996 filed on Aug. 30, 1996 and 208897/1997 filed on Aug. 4, 1997, both of which are incorporated herein by reference in their entirety.

What is claimed as new and desired to be secured by Letters Patent of the United States is:

1. A composition suitable for hair care, comprising:
    (A) at least one basic amino acid derivative represented by formula (1) or a salt thereof:

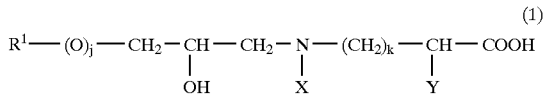 (1)

wherein
$R^1$ is a linear or branched alkyl or alkenyl group having from 8 to 22 carbon atoms;
j is 0;
X is a hydrogen atom or a substituent represented by formula (2):

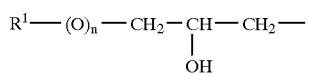 (2)

in which
n is 0 or 1;
k is an integer from 0 to 5, and
when k is 0, Y is a substituent represented by formula (3)

 (3)

in which
m is an integer from 1 to 5, and
Z represents one of the following substituents (a) to (d):

 (a)

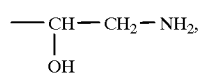 (b)

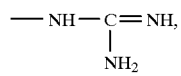 (c)

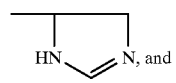 (d)

when k is an integer from 1 to 5, Y represents an amino group; and
(B) at least one higher alcohol containing at least 12 carbon atoms.

2. The composition of claim 1, wherein k is 0.
3. The composition of claim 1, wherein k is an integer from 1 to 5.
4. The composition of claim 1, wherein X is a hydrogen atom.
5. The composition of claim 1, wherein X is the substituent represented by formula (2).
6. The composition of claim 1, wherein the higher alcohol has 12 to 36 carbon atoms.
7. The composition of claim 1, comprising 0.1 to 10% by weight of (A).

8. The composition of claim 1, comprising 0.1 to 30% by weight of (B).
9. The composition of claim 1, comprising 0.1 to 10% by weight of (A) and 0.1 to 30% by weight of (B), wherein the weight ratio of (B) to (A) is 10:100 to 100:0.5.
10. The composition of claim 1, prepared by a process comprising combining (A) and (B).
11. The composition of claim 1, further comprising:
    (C) at least one cationic polymer.
12. The composition of claim 11, comprising 0.1 to 10% by weight of (C).
13. The composition of claim 1, further comprising:
    (D) at least anionic surface active agent, at least one ampholytic surface active agent, or both.
14. The composition of claim 13, comprising 0.1 to 70% by weight of (D).
15. The composition of claim 1, further comprising:
    (C) at least one cationic polymer; and
    (D) at least anionic surface active agent, at least one ampholytic surface active agent, or both.
16. The composition of claim 15, comprising:
    0.1 to 10% by weight of (A);
    0.1 to 30% by weight of (B);
    0.1 to 10% by weight of (C); and
    0.1 to 70% by weight of (D).
17. A composition suitable for hair care obtained by a process comprising combining:
    (A) at least one basic amino acid derivative represented by formula (1) or a salt thereof:

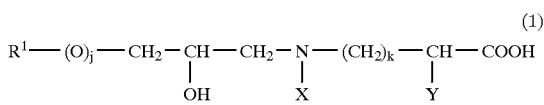 (1)

wherein
$R^1$ is a linear or branched alkyl or alkenyl group having from 8 to 22 carbon atoms;
j is 0;
X is a hydrogen atom or a substituent represented by formula (2):

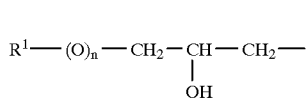 (2)

in which
n is 0 or 1;
k is an integer from 0 to 5, and
when k is 0, Y is a substituent represented by formula (3)

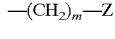 (3)

in which
m is an integer from 1 to 5, and
Z represents one of the following substituents (a) to (d):

 (a)

-continued

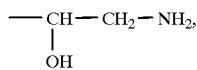 (b)

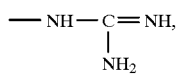 (c)

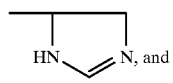 (d)

when k is an integer from 1 to 5, Y represents an amino group; and (B) at least one higher alcohol containing at least 12 carbon atoms;
(C) at least one cationic polymer; and
(D) at least anionic surface active agent, at least one ampholytic surface active agent, or both.

18. The composition of claim 17, wherein (D) comprises at least one anionic surface active agent.

19. A method of conditioning hair, comprising applying the composition of claim 1 to the hair.

20. A method of washing hair, conditioning hair, or both, comprising applying the composition of claim 13 to the hair.

21. A method of washing hair, conditioning hair, or both, comprising applying the composition of claim 17 to the hair.

22. A method of washing hair, conditioning hair, or both, comprising applying the composition of claim 18 to the hair.

* * * * *